(12) United States Patent
Ok et al.

(10) Patent No.: US 7,645,715 B2
(45) Date of Patent: Jan. 12, 2010

(54) BIS-ARYLARYLOXY CATALYTIC SYSTEM FOR PRODUCING ETHYLENE HOMOPOLYMERS OR ETHYLENE COPOLYMERS WITH ALPHA-OLEFINS

(75) Inventors: Myung-Ahn Ok, Daejeon (KR); Jong-sok Hahn, Daejeon (KR); Dae Ho Shin, Daejeon (KR); Sang-Ook Kang, Seoul (KR); Tae Eung Kim, Seoul (KR)

(73) Assignee: SK Energy Co., Ltd., Seoul (KR)

( * ) Notice: Subject to any disclaimer, the term of this patent is extended or adjusted under 35 U.S.C. 154(b) by 0 days.

(21) Appl. No.: 11/738,697

(22) Filed: Apr. 23, 2007

(65) Prior Publication Data
US 2007/0249490 A1 Oct. 25, 2007

(30) Foreign Application Priority Data
Apr. 24, 2006 (KR) .................. 10-2006-0036840

(51) Int. Cl.
C08F 4/642 (2006.01)
C08F 4/6592 (2006.01)
B01J 31/22 (2006.01)

(52) U.S. Cl. ............... 502/152; 502/103; 526/131; 526/160; 526/165; 526/943; 556/53

(58) Field of Classification Search .......... 502/103, 502/152; 526/131, 160, 165, 943
See application file for complete search history.

(56) References Cited

U.S. PATENT DOCUMENTS

| 4,752,597 | A | 6/1988 | Turner |
| 5,043,408 | A | 8/1991 | Kakugo et al. |
| 5,055,438 | A | 10/1991 | Canich |
| 5,079,205 | A | 1/1992 | Canich |
| 5,103,030 | A | 4/1992 | Rohrmann et al. |
| 5,198,401 | A | 3/1993 | Turner et al. |
| 6,329,478 | B1 | 12/2001 | Katayama et al. |
| 2007/0004586 | A1* | 1/2007 | Woo et al. ............ 502/117 |
| 2007/0135297 | A1* | 6/2007 | Woo et al. ............ 502/152 |

FOREIGN PATENT DOCUMENTS

| EP | 0277004 | 8/1988 |
| EP | 0416815 | 3/1991 |
| JP | 63-092621 | 4/1988 |
| JP | 02-084405 | 3/1990 |
| JP | 03-002347 | 1/1991 |
| KR | 10-2001-0074722 | 8/2001 |

OTHER PUBLICATIONS

Nomura et al., Organometallics, vol. 17, pp. 2152-2154 (1998).
Thom et al., Journal of Organometallic Chemistry, vol. 591, pp. 148-162 (1999).
Liu et al., Macromolecules, vol. 34, pp. 4757-4767 (2001).

* cited by examiner

*Primary Examiner*—Caixia Lu
(74) *Attorney, Agent, or Firm*—Darby & Darby P.C.

(57) ABSTRACT

The present invention relates to a bis-arylaryloxy catalyst system for the production of ethylene homopolymers or copolymers with α-olefins, which has high catalytic activity. More particularly, it relates to a transition metal catalyst comprising a group-IV transition metal as a central metal, a cyclopentadiene derivative around the central metal, and two aryloxide ligands substituted with aryl derivatives at the ortho-positions, the ligands not being bridged to each other, as well as a catalyst system comprising said catalyst and an aluminoxane co-catalyst or a boron compound co-catalyst, and a method for producing high-molecular-weight ethylene homopolymers or copolymers with α-olefins using the same.

12 Claims, 2 Drawing Sheets monoclinic, $P2_1/c$, R1 = 0.0498

BIS-ARYLARYLOXY CATALYTIC SYSTEM FOR PRODUCING ETHYLENE HOMOPOLYMERS OR ETHYLENE COPOLYMERS WITH ALPHA-OLEFINS

BACKGROUND OF THE INVENTION

1. Field of the Invention

The present invention relates to a bis-arylphenoxy catalyst system for producing ethylene homopolymers or ethylene copolymers with alpha-olefins, and more particularly to a group-IV transition metal catalyst shown in Formula 1, which comprises a cyclopentadiene derivative around a group-IV transition metal and two aryloxide ligands substituted with aryl derivatives at the ortho-positions, the ligands not being bridged to each other, as well as a catalyst system comprising said bis-arylaryloxy transition metal catalyst and an aluminoxane co-catalyst or a boron compound co-catalyst, and a method for producing ethylene homopolymers or ethylene copolymers with α-olefins using said catalyst:

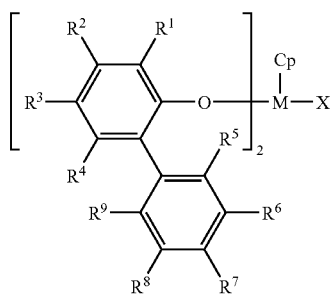

[Formula 1]

wherein M is a group-IV transition metal in the periodic table; Cp is cyclopentadienyl or a derivative thereof, which can $\eta^5$-bind to the metal center; $R^1$, $R^2$, $R^3$, $R^4$, $R^5$, $R^6$, $R^7$, $R^8$ and $R^9$ on the arylphenoxide ligands are each independently a hydrogen atom, a halogen atom, a C1-C20 linear or nonlinear alkyl group optionally substituted with at least one halogen atoms, a silyl group containing a C1-C20 linear or nonlinear alkyl group optionally substituted with at least one halogen atoms, a C6-C30 aryl group optionally substituted with at least one halogen atom, an C7-C30 arylalkyl group optionally substituted with at least one halogen atom, an alkoxy group having a C1-C20 linear or nonlinear alkyl group optionally substituted with at least one halogen atoms, a siloxy group having C3-C20 alkyl or C6-C20 aryl, an amido or phosphido group having a C1-C20 hydrocarbon group, or a mercapto or nitro group having C1-C20 alkyl, and may also optionally bind to each other to form a ring; and X is selected from the group consisting of an halogen atom, a C1-C20 alkyl group other than a Cp derivative, a C7-C30 arylalkyl group, an alkoxy group having a C1-C20 alkyl group, a siloxy group having C3-C20 alkyl, and an amido group having a C1-C20 hydrocarbon group.

2. Description of the Prior Art

In the production of ethylene homopolymers or ethylene copolymers with α-olefins according to the prior art, a so-called Ziegler-Natta catalyst system consisting of a main catalyst component of a titanium or vanadium compound and a co-catalyst component of an alkyl aluminum compound has generally been used. The Ziegler-Natta catalyst system shows high activity for ethylene polymerization, but has problems in that, due to the heterogeneity of catalytic active sites, the molecular weight distribution of produced polymers is generally wide, and the composition distribution is not uniform, particularly in copolymers of ethylene with α-olefin.

Recently, a so-called metallocene catalyst system consisting of a metallocene compound of periodic table group-IV transition elements (e.g., titanium, zirconium, hafnium, etc.) and co-catalyst methylaluminoxane has been developed. Because the metallocene catalyst system is a homogeneous catalyst having a single species of catalytic active site, it has a characteristic in that it can produce polyethylene having a narrow molecular weight distribution and uniform composition distribution, compared to the existing Ziegler-Natta catalyst system. For example, European Patent Publication No. 320,762 or 277,004 and Japanese Patent Publication No. Sho 63-092621, Hei 02-84405 or Hei 03-2347 disclose a metallocene compound such as Cp2TiCl2, Cp2ZrCl2, Cp2ZrMeCl, Cp2ZrMe2 or ethylene (IndH4)2ZrCl2, activated with co-catalyst methylaluminoxane, that can polymerize ethylene at high activity to produce polyethylene having a molecular weight distribution (Mw/Mn) of 1.5-2.0. However, it is known that it is difficult for said catalyst system to obtain high-molecular-weight polymers, and said catalyst system is unsuitable for the production of high-molecular-weight polymers having a weight-average molecular weight (Mw) of more than 100,000, because, particularly when it is applied in solution polymerization conducted at a high temperature of more than 140° C., the polymerization activity thereof will be rapidly reduced and β-dehydrogenation reactions will predominate.

Meanwhile, as a catalyst capable of producing high-molecular-weight polymers at high catalytic activity in solution polymerization conditions for ethylene homopolymerization or ethylene copolymerization with α-olefins, a so-called "constrained geometry catalyst" (single active site catalyst) having a transition metal connected to a ring structure has been reported. European Patent Publication Nos. 0416815 and 0420436 disclose an example in which an amide group is connected to a cyclopentadienyl ligand in the form of a ring structure, and European Patent Publication No. 0842939 shows an example of a catalyst in which a phenol compound as an electron donor compound is connected with a cyclopentadiene ligand in the form of a ring structure. However, because the yield of ring formation reaction between the ligand and the transition metal compound in a step of synthesizing this constrained geometry catalyst is very low, it is very difficult to commercially use the constrained geometry catalyst.

On the other hand, an example of a catalyst, which is a non-metallocene catalyst, but not a constrained geometry catalyst, and, at the same time, can be used in high-temperature conditions, is disclosed in U.S. Pat. No. 6,329,478 and Korean Patent Publication No. 2001-0074722. In these patents, it can be seen that a single active site catalyst having a phosphinimine compound as a ligand shows high ethylene conversion in the copolymerization of ethylene with α-olefin in a high-temperature solution polymerization condition of more than 140 °C. However, for the synthesis of the phosphinimine ligand, a restrictive phosphine compound should be used, which is very difficult to use for general-purpose olefin polymers, because it is harmful to the human body and to the environment. U.S. Pat. No. 5,079,205 discloses an example of a catalyst having a bis-phenoxide ligand, and U.S. Pat. No. 5,043,408 discloses an example of a catalyst having a chelated bisphenoxide ligand, but these catalysts have too low activity, and thus are difficult to commercially use for the production of ethylene homopolymers or ethylene copolymers with α-olefins, which is conducted at high temperatures.

In addition to the above examples, an example relating to the synthesis of a phenolic ligand as a non-metallocene catalyst and the use thereof in polymerization was reported in the literature "*Organometallics* 1998, 17, 2152 (Nomura, et al.)", but this example is limited to an isopropyl group, a simple alkyl substituent, and is thus different from an arylaryloxy catalyst according to the present invention with respect to structural and electronic properties. Also, there is no mention of polymerization reactivity at high temperature. On the other hand, the case of an arylphenoxy ligand is mentioned in the literature "*J. Organomet. Chem.* 1999, 591, 148 (Rothwell, P. et al.)", but this literature did not recognize the effect of an aryl substituent at the ortho-position and does not show the concrete application of the ligand as a catalyst for polymerization.

SUMMARY OF THE INVENTION

The present inventors have conducted extensive studies to overcome the above-described problems and, as a result, have found that a non-bridged transition metal catalyst comprising a cyclopentadiene derivative and two aryloxide ligands substituted with an aryl derivative at the two ortho-positions shows excellent catalytic activity in the polymerization of ethylene. On the basis of this fact, the present inventors have developed a catalyst enabling high-molecular-weight ethylene homopolymers or copolymers with α-olefins to be produced at high activity in a polymerization process conducted at high temperatures, thereby completing the present invention.

Accordingly, it is an object of the present invention to provide a single-active-site catalyst which is synthesized in a very economical manner using eco-friendly raw materials and has excellent catalytic activity in ethylene polymerization, as well as a polymerization method enabling ethylene homopolymers or ethylene/α-olefin copolymers, having various physical properties, to be produced using said catalyst component economically from a commercial point of view.

To achieve the above objects, according to one aspect of the present invention, there is provided a bis-arylphenoxy transition metal catalyst shown in Formula 1, which comprises a cyclopentadiene derivative around a transition metal and two aryloxide ligands substituted with aryl derivatives at the ortho-positions, the ligands not being bridged to each other:

[Formula 1]

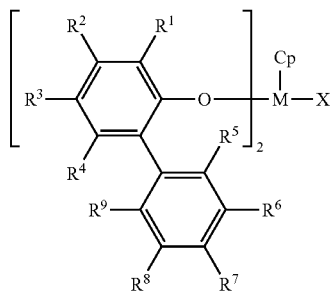

wherein M is a group-IV transition metal in the periodic table; Cp is cyclopentadienyl or a derivative thereof, which can form an $\eta^5$-bond with the central metal; $R^1$, $R^2$, $R^3$, $R^4$, $R^5$, $R^6$, $R^7$, $R^8$ and $R^9$ on the arylphenoxide ligands are each independently a hydrogen atom, a halogen atom, a C1-C20 linear or nonlinear alkyl group optionally substituted with at least one halogen atom, a silyl group containing a C1-C20 linear or nonlinear alkyl group optionally substituted with at least one halogen atom, a C6-C30 aryl group optionally substituted with at least one halogen atom, an C7-C30 arylalkyl group optionally substituted with at least one halogen atom, an alkoxy group having a C1-C20 linear or nonlinear alkyl group optionally substituted with at least one halogen atom, a siloxy group having C3-C20 alkyl or C6-C20 aryl, an amido or phosphido group having a C1-C20 hydrocarbon group, or a mercapto or nitro group having C1-C20 alkyl, these substituents also optionally binding to each other to form a ring; and X is selected from selected from the group consisting of a halogen atom, a C1-C20 alkyl group other than a Cp derivative, a C7-C30 arylalkyl group, an alkoxy group having a C1-C20 alkyl group, a siloxy group having C3-C20 alkyl, and an amido group having a C1-C20 hydrocarbon group.

According to another aspect of the present invention, there is provided a catalyst system comprising said transition metal catalyst and an aluminum or boron compound as a co-catalyst.

According to still another aspect of the present invention, there is provided a method for producing ethylene polymers using said transition metal catalyst.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
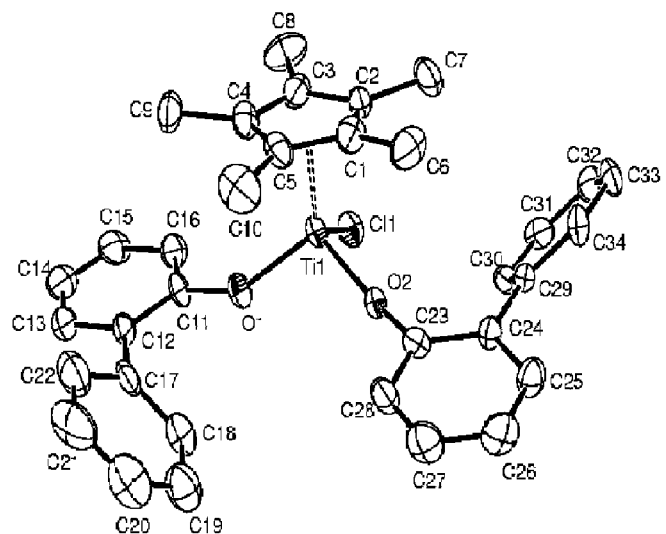
FIG. 1 is shows the crystalline structure of a bis(2-phenylphenoxy)(pentamethylcyclopentadienyl)titanium(IV) chloride catalyst according to Preparation Example 5 of the present invention 1.

Hereinafter, the present invention will be described in further detail.

M in the transition metal catalyst shown in Formula 1 above is preferably titanium, zirconium or hafnium. Also, Cp is a cyclopentadiene anion or a derivative thereof, which can form a $\eta^5$ bond with the central metal. More specifically, examples of Cp include cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, and isopropylfluorenyl.

In the definition of $R^1$, $R^2$, $R^3$, $R^4$, $R^5$, $R^6$, $R^7$, $R^8$ and $R^9$ present on the arylphenoxide ligands, examples of the halogen atom include a fluorine atom, chlorine atom, bromine atom and iodine atom. Also, examples of the C1-C20 alkyl group include a methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, n-eicosyl group and the like, and preferable examples thereof include a methyl group, ethyl group, isopropyl group, tert-butyl group and amyl group. Also, examples of the C1-C20 alkyl group optionally substituted with at least one halogen atom include a fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group and the like, preferred being a trifluoromethyl group. Also, in said substituents on the arylphenoxide ligands, examples of the silyl group substituted with C1-C20 alkyl include a methylsilyl group, ethylsilyl group, phenylsilyl group, dimethylsilyl group, diethylsilyl group, diphenylsilyl group, trimethylsilyl group, triethylsilyl group, tri-n-propylsilyl group, triisopropylsilyl group, tri-n-butylsilyl group, tri-sec-butyl silyl group, tri-tert-butylsilyl group, tri-isobutylsilyl group, tert-butyldimethylsilyl group, tri-n-pentylsilyl group, tri-n-hexylsilyl group, tricyclohexylsilyl group, triphenylsilyl group and the like, and preferable examples thereof include a trimethylsilyl group, tert-butyldimethylsilyl group and triphenylsilyl group. Examples of the C6-C30 aryl group include a phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group and the like, and preferably a phenyl group, naphthyl group, biphenyl group, 2-isopropylphenyl group, 3,5-xylyl group and 2,4,6-trimethylphenyl group. Also, examples of the C7-C30 arylalkyl group include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,5-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-tetradecylphenyl)methyl group, naphthylmethyl group, anthracenylmethyl group and the like, and a benzyl group is more preferable. Also, examples of the C1-C20 alkoxy group include a methoxy group, ethoxy group, n-propoxy group, isopropoxy group, n-butoxy group, sec-butoxy group, tert-butoxy group, n-pentyloxy group, n-hexyloxy group, n-octyloxy group, n-dodecyloxy group, n-pentadecyloxy group, n-eicosyl oxy group and the like, and preferred examples thereof include a methoxy group, ethoxy group, isopropoxy group and tert-butoxy group. Also, examples of the siloxy group substituted with C3-C20 alkyl or C6-C20 aryl include a trimethylsiloxy group, triethylsiloxy group, tri-n-propylsiloxy group, triisopropylsiloxy group, tri-n-butylsiloxy group, tri-sec-butylsiloxy group, tri-tert-butylsiloxy, triisobutylsiloxy group, tert-butyldimethylsiloxy group, tri-n-pentylsiloxy group, tri-n-hexylsiloxy group, tricyclohexylsiloxy group, triphenylsiloxy group and the like, and preferably a trimethylsiloxy group, tert-butyldimethylsiloxy group and triphenylsiloxy group, and these substituents may be substituted with at least one halogen atoms. Also, examples of the amido group or phosphido group having a C1-C20 hydrocarbon group include a dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, dibenzylamide group, methylethylamide group, methylphenylamide group, benzylhexylamide group, bistrimethylsilylamino group, bis-tert-butyldimethylsilylamino group and the like, and phosphido groups substituted with the same alkyl group as used in the above-exemplified amido groups, and preferred examples thereof include a dimethylamino group, diethylamino group and diphenylamide group. In addition, examples of the C1-C20 mercapto group include methylmercaptan, ethylmercaptan, propylmercaptan, isopropylmercaptan, 1-butylmercaptan, isopentylmercaptan and the like, and preferably ethylmercaptan and isopropylmercaptan.

In the definition of X in the transition metal catalyst shown in Formula 1 above, examples of the halogen atom include a fluorine atom, chlorine atom, bromine atom, iodine atom and the like. Also, in the definition of X, examples of the C1-C20 alkyl group other than a Cp derivative include a methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, n-eicosyl group and the like, and preferably a methyl group, ethyl group, isopropyl group, tert-butyl group and amyl group. Also, examples of the C7-C30 arylalkyl group in the definition of X include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl) methyl group, (4,5-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl) methyl group, (n-pentylphenyl)methyl group, (neopentylphenyl)methyl group, (n-hexylphenyl)methyl group, (n-octylphenyl)methyl group, (n-decylphenyl)methyl group, (n-tetradecylphenyl)methyl group, naphthylmethyl group, anthracenylmethyl group and the like, preferred being a benzyl group. Also, examples of the C1-C20 alkoxy group in the definition of X include a methoxy group, ethoxy group, n-propoxy group, isopropoxy group, n-butoxy group, sec-butoxy group, tert-butoxy group, n-pentyloxy group, n-hexyloxy group, n-octyloxy group, n-dodecyloxy group, n-pentadecyloxy group, n-eicosyl oxy group and the like, and preferred examples thereof include a methoxy group, ethoxy group, isopropoxy group and tert-butoxy group. Also, examples of the siloxy group substituted with C3-C20 alkyl include a trimethylsiloxy group, triethylsiloxy group, tri-n-propylsiloxy group, triisopropylsiloxy group, tri-n-butylsiloxy group, tri-sec-butylsiloxy group, tri-tert-butylsiloxy group, triisobutylsiloxy group, tert-butyldimethylsiloxy group, tri-n-pentylsiloxy group, tri-n-hexylsiloxy group, tricyclohexylsiloxy group the like, and preferably a trimethylsiloxy group and tert-butyldimethylsiloxy group. In addition, in the definition of X, examples of the amido group or phosphido group having a C1-C20 hydrocarbon group include a dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, dibenzylamide group, methylethylamide group, methylphenylamide group, benzylhexylamide group, bistrimethylsilylamino group, bis-tert-butyldimethylsilylamino group and the like, and phosphido groups substituted with the same alkyl group as used in the above-exemplified amido groups, and preferred examples thereof include a dimethylamino group, diethylamino group and diphenylamide group.

Meanwhile, in order for the transition metal catalyst of Formula 1 to be used as an active catalytic component in the production of ethylene homopolymers or ethylene copolymers with α-comonomers, the transition metal catalyst can preferably act with an aluminoxane compound or boron compound as a co-catalyst, which can act as a counterion (i.e., anion) which has a weak bonding force while cationizing the central metal by extracting the ligand X from the transition metal complex.

As the aluminoxane compound in the present invention, a generally well-known aluminoxane represented by Formula 2 or 3 below is mainly used:

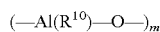  [Formula 2]

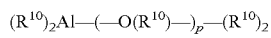  [Formula 3]

wherein $R^{10}$ is a C1-C20 alkyl group, preferably a methyl group or isobutyl group, and m and p are each independently an integer ranging from 5 to 20.

Regarding the blending ratio between the two components for use of the inventive transition metal catalyst as an actual active catalyst, the molar ratio of central metal:aluminum is preferably 1:20 to 1:10,000, and more preferably 1:50 to 1:5,000.

Also, the boron compound which can be used as a co-catalyst in the present invention can be selected from compounds represented by Formulas 4 to 6 below, as can be seen in U.S. Pat. No. 5,198,401:

  [Formula 4]

  [Formula 5]

  [Formula 6]

wherein B is a boron atom; $R^{11}$ is an unsubstituted phenyl group or a phenyl group substituted with 3-5 substituents selected from a C1-C4 alkyl group and alkoxy group substituted or unsubstituted with a halogen atom; $R^{12}$ is a cyclic C5-C7 aromatic cation or alkyl-substituted aromatic cation, for example, a triphenylmethyl cation; Z is a nitrogen or phosphorus atom; $R^{13}$ is a C1-C4 alkyl radical or an anilinium radical substituted with two C1-C4 alkyl groups together with a nitrogen atoms; and q is an integer of 2 or 3.

Preferred examples of the boron co-catalyst include tris (pentafluorophenyl)borane, tris(2,3,5,6-tetrafluorophenyl) borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenyltris(pentafluorophenyl)borate, and tetrakis(3,5-bistrifluoromethylphenyl)borate. Also, specific combinations of these include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis (pentafluorophenyl)borate, tri-n-butylammonium tetrakis (pentafluorophenyl)borate, tri(n-butyl)ammonium tetrakis (3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl) borate, diisopropylammonium tetrakis(pentafluorophenyl) borate, dicyclohexylammonium tetrakis(pentafluorophenyl) borate, triphenylphosphonium tetrakis(pentafluorophenyl) borate, tri(methylphenyl)phosphonium tetrakis (pentafluorophenyl) borate, tri(dimethylphenyl) phosphonium tetrakis(pentafluorophenyl)borate and the like, and among them, triphenylmethyl tetrakis(pentafluorophenyl) borate, N,N-dimethylanilinium tetrakis(pentafluorophenyl)borate and tris(pentafluorophenyl)borane are most preferable.

In the catalyst system comprising the boron co-catalyst, the molar ratio of central metal:boron atom is preferably 1:0.01 to 1:100, and more preferably 1:0.5 to 1:5.

The transition metal catalyst system according to the present invention may, if necessary, comprise a mixture of said boron compound with an organoaluminum compound or a mixture of said boron compound with said aluminoxane. In this case, the aluminum compound is used to remove a polar compound acting as catalytic poison in a reaction solvent, but may also act as an alkylating agent, if X of the catalyst component is halogen.

The organoaluminum compound is represented by Formula 7 below:

$(R^{14})_r Al(E)_{3-r}$ [Formula 7]

wherein $R^{14}$ is an alkyl group having 1 to 8 carbon atoms, E is a hydrogen or halogen atom, and 'r' is an integer ranging from 1 to 3.

Specific examples of the organoaluminum compound, which can be used in the present invention, include trialkylaluminums, such as trimethylaluminum, triethylaluminum, tripropylaluminum, triisopropylaluminum, and trihexylaluminum; tricycloalkylaluminums, such as tricyclohexylaluminum and tricyclooctylaluminum; dialkylaluminum chlorides, such as dimethylaluminum chloride, diethylaluminum chloride, dipropylaluminum chloride, diisobutylaluminum chloride, and dihexylaluminum chloride; alkylaluminum dichlorides, such as methylaluminum dichloride, ethylaluminum dichloride, propylaluminum dichloride, isobutylaluminum dichloride, and hexylaluminum dichloride; and dialkylaluminum hydrides, such as dimethylaluminum hydride, diethylaluminum hydride, dipropylaluminum hydride, diisobutylaluminum hydride, and dihexylaluminum hydride; preferably trialkylaluminum, and more preferably triethylaluminum and triisobutylaluminum.

Herein, the molar ratio of central metal:aluminum atom is preferably 1:0.1-100:10-1000, and more preferably 1:0.5-5: 25-500.

As another aspect of the present invention, the method for producing ethylene polymers using said transition metal catalyst systems is carried out by bringing said transition metal catalyst, said co-catalyst, and an ethylene monomer, if necessary, a vinyl comonomer, into contact with each other in the presence of a suitable organic solvent. In this case, the transition metal catalyst and co-catalyst components can be separately added into a reactor. Alternatively, a previously prepared mixture thereof can be added into the reactor. Herein, mixing conditions such as the order of addition, temperature or concentration are not specifically limited.

A preferred organic solvent which can be used in said production method is a C3-C20 hydrocarbon, and specific examples thereof include butane, isobutane, pentane, hexane, heptane, octane, isooctane, nonane, decane, dodecane, cyclohexane, methylcyclohexane, benzene, toluene, xylene and the like.

Specifically, in the production of high-density polyethylene (HDPE) as an ethylene homopolymer, ethylene as a monomer is used alone, and the pressure of ethylene suitable for the present invention is preferably 1-1,000 atm, and more preferably 10-150 atm. Also, the polymerization of ethylene is carried out at a temperature of 60-300° C., and preferably 80-250° C.

In the production of a copolymer of ethylene with α-olefin, α-olefin having 3 to 18 carbon atoms can be used as a comonomer together with ethylene, and can preferably be selected from the group consisting of propylene, 1-butene, 1-pentene, 4-methyl-1-pentene, 1-hexene, 1-ocetene, 1-decene, 1-dodecene, 1-hexadecene, and 1-octadecene. More preferably, ethylene can be copolymerized with 1-butene, 1-hexene, 1-octene or 1-decene. In this case, the preferred pressure and polymerization temperature of ethylene are the same as described above for the production of high-density polyethylene (HDPE), and an ethylene copolymer produced according to the inventive method generally has an ethylene content of more than 60 wt %, and preferably 75 wt %. Linear low-density polyethylene (LLDPE) produced using the C4-C10 α-olefin as a comonomer as described above has a density ranging from 0.910 g/cc to 0.940 g/cc, and the inventive method can also be applied for the production of very low-density or ultra-low-density polyethylene (VLDPE or ULDPE) having a density of less than 0.910 g/cc. Also, in the production of an ethylene homopolymer or copolymer according to the present invention, hydrogen can be used as an agent for controlling the molecular weight of the polymer, and the polymer generally has a weight-average molecular weight (Mw) of 50,000-500,000 g/mol.

Because the catalyst system suggested in the present invention is present in homogeneous form in a reactor, it is preferably used in a solution polymerization process which is carried out at a temperature higher than the melting point of the relevant polymer. However, as disclosed in U.S. Pat. No. 4,752,597, a heterogeneous catalyst system formed by supporting said transition metal catalyst and co-catalyst on a porous metal oxide support can also be used in a slurry polymerization or vapor-phase polymerization process.

EXAMPLE

Hereinafter, the present invention will be described in detail with reference to examples, but these examples are not to be construed to limit the scope of the present invention.

Unless specified otherwise, all experiments for synthesizing ligands and catalysts were conducted using standard Schlenk or glovebox techniques in a nitrogen atmosphere, and organic solvents used in reactions were refluxed in the presence of a sodium metal and benzophenone to remove water, and distilled just before use. The $^1$H-NMR analysis of synthesized ligands and catalysts was performed using Varian Oxford 300 MHz spectroscopy at room temperature. The molecular weight of synthesized catalyst compounds was measured using Quatro micro MS (Micromass) in an APCI-mode ionization source at a direct effusion flowrate of 20 ml/min.

Polymerization solvent cyclohexane was used after sufficiently removing water, oxygen and other catalytic poison substances therefrom by passing it through a column packed with silica gel, molecular sieve 5A and activated alumina and bubbling it with high-purity nitrogen. Produced polymers were analyzed in the following manner.

1. Melt index (MI)

This was measured in accordance with ASTM D 2839.

2. Density

This was measured using a density gradient column in accordance with ASTM D 1505.

3. Analysis of melting point (Tm)

Melting point was measured using Dupont DSC2910 at a heating rate of 10° C./min in a nitrogen atmosphere.

4. Molecular weight and molecular weight distribution

Measurement was conducted using PL210 GPC equipped with PL mixed-BX2+preCol at 135° C. at a rate of 1.0 ml/min in the presence of a 1,2,3-trichlorobenzene solvent. A PL polystyrene standard was used to calibrate molecular weight.

5. Content (wt %) of α-olefin in copolymer

This was measured using a Bruker DRX500 FT-NMR spectrometer at 125 MHz in a mixed solvent of 1,2,4-trichlorobenzene/$C_6D_6$ (7/3 w/w) at 120° C. in the $^{13}$C-NMR mode (see Rinaldi, P. L., *Macromolecules,* 2001, 34, 4757).

Preparation Example 1

Synthesis of 2-phenyl-4-fluorophenol 2-bromo-4-fluorophenol (4.16 g, 20.32 mmol, Aldrich) was added into the flask, and then nitrogen was introduced thereto. Palladium acetate (0.22 g, 1.02 mmol), potassium phosphate (21.00 g, 91.19 mmol), phenylboronic acid (2.97 g, 24.36 mmol) and triphenylphosphine (0.80 g, 3.06 mmol) were additionally added into the flask. DME (32 ml) and distilled water (8 ml) were added into, followed by stirring well. The mixture was heated to 50° C. and then stirred for 6 hours. After completion of the reaction, the reaction product was cooled to room temperature, and the organic layer was separated with ammonium chloride diethylether (10 ml×3) and distilled water. Then, magnesium sulfate was added to the collected organic layer, followed by stirring for 30 minutes. The mixture was filtered and treated to remove volatile material, thus obtained material was cooled to −78° C. followed by slowly adding borontribromide (30.48 ml, 1.0M in methylene chloride Aldrich) dropwise. After completion of the addition, the mixture was maintained at that temperature for 1 hour, and then warmed to room temperature and stirred for 12 hours. Then, the organic layer was separated with ammonium chloride diethylether (10 ml×3) and distilled water from the obtained material. Subsequently, magnesium sulfate was added to the collected organic layer, followed by stirring for 30 minutes. After filtering, removing volatile components, and the residue was passed through a silica gel chromatography column using a mixed solvent of hexane and methylene chloride (1.5:1) as moving phase. From obtained mixture, volatile components were removed to yield 3.76 g of 2-phenyl-4-fluorophenol as white solid.

Yield: 98%, $^1$H-NMR (CDCl$_3$) δ=1.54 (s, 15H), 6.92-7.52 (m, 8H)

Preparation Example 2

Synthesis of bis(pentamethylcyclopentadienyl)(2-phenyl-4-fluorophenoxy)titanium(IV) chloride After 1.90 g (10.09 mmol) of 2-phenyl-fluorophenol was dissolved with 80 ml of diethylether, 4.8 ml of butyl lithium (2.5M hexane solution) was slowly added thereon dropwise at 0° C. After reacting for 5 hours at the room temperature, a solution of trichloro(penta methylcyclopentadienyl)titanium (IV) (1.64 g, 5.5 mmol) in 10 ml diethylether was slowly added dropwise at −78° C. Thus obtained material was stirred for 12 hours at the room temperature followed by filtering, and then volatile components were removed followed by recrystallizing with mixing solution of toluene/hexane at −35° C. to yield 2.54 g of an orange-colored solid.

Yield: 85%, $^1$H-NMR ($C_6D_6$) δ=1.46 (s, 15H), 6.65-7.57 (m, 8H)

Preparation Example 3

Synthesis of 2-(4-trifluoromethylphenyl)phenol 4-trifluoromethylbromobenzene (4.57 g, 20.32 mmol, Aldrich) was added into the flask, and then nitrogen was introduced thereto. Palladium acetate (0.22 g, 1.02 mmol), potassium phosphate (21.00 g, 91.19 mmol), 2-methoxy boronic acid (3.71 g, 20.32 mmol, Aldrich) and triphenylphosphine (0.80 g, 3.06 mmol) were additionally added into the flask. DME (32 ml) and distilled water (8 ml) were added into, followed by stirring well. The mixture was heated to 50° C. and then stirred for 6 hours. After completion of the reaction, the reaction product was cooled to room temperature, and the organic layer was separated with ammonium chloride diethylether (10 ml×3) and distilled water. Then, magnesium sulfate was added to the collected organic layer, followed by stirring for 30 minutes. Mixture was filtered and treated to remove volatile material. Thus obtained material was introduced to dried flask followed by being dissolved with methylene chloride. After temperature of the mixture was lowered to −78° C. followed by slowly adding borontribromide (30.48 ml, 1.0M in methylene chloride Aldrich) dropwise. When the addition was completed, the mixture was maintained at that temperature for 1 hour, and then warmed to room temperature and stirred for 12 hours. Then, the organic layer was separated with ammonium chloride diethylether (10 ml×3) and distilled water from the obtained material. Subsequently, magnesium sulfate was added to the collected organic layer, followed by stirring for 30 minutes. After filtering, removing volatile components, and the residue was passed through a silica gel chromatography column using a mixed solvent of hexane and methylene chloride (2:1) as moving phase. From obtained mixture, volatile components were removed to yield 4.55 g of 2-(4-trifluoromethylphenyl)phenol as white solid.

Yield: 90%, $^1$H-NMR (CDCl$_3$) δ=1.54 (s, 1H), 6.58-7.75 (m, 8H)

Preparation Example 4

Synthesis of bis(pentamethyl cyclopentadienyl)((2-(4-trifluoromethyl)phenyl)phenoxy)titanium(IV) chloride After 2.42 g (10.16 mmol) of 2-phenyl-fluorophenol was dissolved with 80 ml of diethylether, 4.8 ml of butyl lithium (2.5M hexane solution) was slowly added thereon dropwise at 0° C. After reacting for 5 hours at the room temperature, a solution of trichloro(penta methylcyclopentadienyl)titanium (IV) (1.64 g, 5.5 mmol) in 10 ml diethylether was slowly added dropwise at −78° C. Thus obtained material was stirred for 12 hours followed by filtering, and then volatile components were removed followed by recrystallizing with mixing solution of toluene/hexane at −35° C. to yield 2.88 g of an orange-colored solid.

Yield: 82%, $^1$H-NMR ($C_6D_6$) δ=1.59 (s, 15H), 6.95-7.85 (m, 8H)

Preparation Example 5

Figure 2:
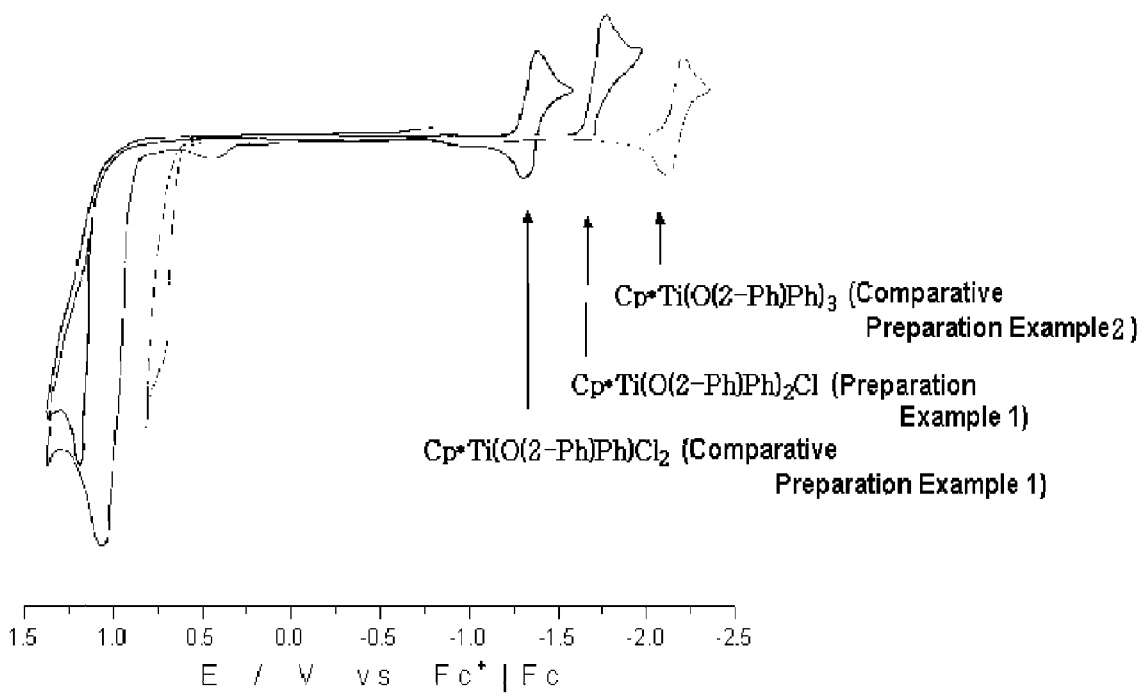
FIG. 2 comparatively shows the cyclic voltammograms of bis(2-phenylphenoxy)(pentamethylcyclopentadienyl)titanium(IV) chloride, (2-phenylphenoxy)(pentamethylcyclopentadienyl)titanium(IV) dichloride, and tris(2-phenylphenoxy)(pentamethylcyclopentadienyl)titanium(IV) catalysts, according to Preparation Example of this invention and Comparative Preparation Examples.

Synthesis of bis(2-phenylphenoxy)(pentamethylcyclopentadienyl)titanium(IV) chloride 2-methylphenol (1.72 g, 10.1 mmol, Aldrich, 99%) was added into a dry flask, in which it was dissolved in 40 ml toluene and then cooled to 0° C. with stirring well. To the solution, N-butyllithium (4.8 ml, 2.5M hexane solution, Aldrich) was slowly added dropwise. After completion of the addition, the mixture was maintained at that temperature for 1 hour, and then warmed to room temperature and stirred for 12 hours. After the temperature of the mixture was lowered to 0° C., a solution of pentamethylcyclopentadienyl titanium trichloride (1.64 g, 5.5 mmol) in 10 ml toluene was slowly added dropwise thereto. After completion of the addition, the mixture was maintained at that temperature, and then warmed to room temperature and stirred for one additional hour. The temperature of the reactor was elevated to 90° C., followed by reaction for 12 hours. The obtained mixture was filtered, treated to remove volatile material, and recrystallized with a mixed solvent of toluene and hexane at −35° C., thus obtaining 2.3 g of an orange-colored solid. The crystalline structure of the above-prepared catalyst is shown in FIG. 1, and the cyclic voltammogram thereof is shown in FIG. 2.

Yield: 75%, $^1$H-NMR ($C_6D_6$) δ=1.54 (s, 15H), 6.74-7.16 (m, 9H) ppm Mass (APCI mode, m/z): 558.

Preparation Example 6

Synthesis of 4-methyl-2-(2'-isoprophenyl)phenol 2-bromo-4-methylanisole (4.08 g, 20.3 mmol) was added into a flask. Then, 2-isopropylphenylboronic acid (5.0 g, 30.5 mmol), palladium acetate (0.22 g, 1.0 mmol), triphenylphosphin (0.80 g, 3.1 mmol) and potassium phosphate (21.0 g, 91.2 mmol) were added thereto in a nitrogen atmosphere, after which 32 ml of dimethoxyethane and 8 ml of distilled water were added. The mixture was heated to 50° C. and then stirred for 6 hours. After completion of the reaction, the reaction product was cooled to room temperature, and the organic layer was separated with ammonium chloride diethylether (10 ml×3) and distilled water, and then dried with magnesium sulfate. The dried material was filtered and treated to remove volatile material, thus obtaining 5.4 g of 4-methyl-2-(2'-isoprophenyl)anisole as a gray solid. The obtained anisole was dissolved in 40 ml methylene chloride without undergoing a separate purification process, and 30.5 ml boron tribromide (1.0M methylene chloride solution) was added dropwise at −78° C. to the solution. Then, the mixture was slowly warmed to room temperature and allowed to react for 12 hours. After completion of the reaction, the organic layer was separated with diethylether (10 ml×3) and water, the collected organic layer was dried and treated under reduced pressure to remove volatile components, and the residue was purified using a silica gel chromatography column in a mixed solvent of hexane and methylene chloride (1.5:1), yielding 4.32 g of 4-methyl-2,6-(2'-isopropylphenyl) phenol as a white solid.

Yield: 93%, $^1$H-NMR ($CDCl_3$) δ=1.10-1.21 (q, 6H), 2.33 (s, 3H), 2.91 (m, 1H), 4.63 (s, 1H), 6.87-7.51 (m, 7H) ppm.

Preparation Example 7

Synthesis of bis(4-methyl-2-(2'-isopropylphenyl) phenoxy)pentamethylcyclopentadienyl)titanium(IV) chloride 4-methyl-2-(2'-isopropylphenyl)phenol (2 g, 8.8 mmol) and sodium hydride (636 mg, 26.5 mmol) were dissolved in 20 ml toluene and then allowed to react under reflux for 4 hours. Then, the reaction solution was cooled to room temperature, after which a solution of (pentamethylcyclopentadienyl)titanium(IV) trichloride (1.15 g, 4.0 mmol) in 5 ml toluene was slowly added dropwise, and the mixture was allowed to react under reflux. After completion of the reaction, the reaction product was treated to remove volatile material, washed with purified hexane, recrystallized with hexane at −35° C., filtered, and dried under reduced pressure, yielding 1.65 g of an orange-colored solid.

Yield: 61%, $^1$H-NMR ($C_6D_6$) δ=0.96-1.07 (m, 6H), 1.54 (s, 15H), 1.72 (s, 3H), 2.76 (m, 1H), 6.76-7.27 (m, 7H) ppm. Mass (APCI mode, m/z): 670.

Example 1

Into a 500-ml stainless steel reactor which was sufficiently dried and then charged with nitrogen, 300 ml of n-heptane was added and 0.5 ml of a solution of 200 mM triisobutylaluminum (Aldrich) in n-heptane was then added. Then, after the temperature of the reactor was elevated to 140° C., 0.2 ml of bis(pentamethylcyclopentadienyl) (2-pheny-4-fluorolphenoxy)titanium(IV) chloride (5 mM toluene solution) synthesized in Preparation Example 2 and 0.3 ml of a toluene solution of 5 mM triphenylmethylinium tetrakis (pentafluorophenyl)borate (99%, Boulder Scientific) were sequentially added into the reactor. Then, the reactor was charged with ethylene until the pressure within the reactor reached 30 kg/cm$^2$. Ten minute after the start of the reaction, 10 ml of ethanol containing 10 vol % aqueous hydrochloric acid solution was added to terminate the polymerization. Then, the polymerization product was stirred in 1500 ml of ethanol for 4 hours, and the reaction product was filtered and separated. The collected reaction product was dried in a vacuum oven at 60° C. for 8 hours, yielding 10.5 g of a polymer. The polymer had a melting point of 138.0° C., melt index of less than 0.017 g/10 min, and when analyzed using gel chromatography, it showed a weight-average molecular weight (Mw) of 256,300 g/mol and a molecular weight distribution (Mw/Mn) of 2.25.

Example 2

Into a 500-ml stainless steel reactor which was sufficiently dried and then charged with nitrogen, 300 ml of n-heptane was added and 0.5 ml of a solution of 200 mM triisobutylaluminum (Aldrich) in n-heptane was then added. Then, after the temperature of the reactor was elevated to 140° C., 0.2 ml of bis(pentamethylcyclopentadienyl)((2-(4-trifluoromethyl) phenyl)phenoxy)titanium(IV) chloride (5 mM toluene solution) synthesized in Preparation Example 4 and 0.3 ml of a toluene solution of 5 mM triphenylmethylinium tetrakis(pentafluorophenyl)borate (99%, Boulder Scientific) were sequentially added into the reactor. Then, the reactor was charged with ethylene until the pressure within the reactor reached 30 kg/cm$^2$. Ten minute after the start of the reaction, 10 ml of ethanol containing 10 vol % aqueous hydrochloric acid solution was added to terminate the polymerization. Then, the polymerization product was stirred in 1500 ml of ethanol for 4 hours, and the reaction product was filtered and separated. The collected reaction product was dried in a vacuum oven at 60° C. for 8 hours, yielding 10.6 g of a polymer. The polymer had a melting point of 137.0° C., melt index of less than 0.023 g/10 min, and when analyzed using gel chromatography, it showed a weight-average molecular weight (Mw) of 213,400 g/mol and a molecular weight distribution (Mw/Mn) of 2.33.

Example 3

Into a 500-ml stainless steel reactor which was sufficiently dried and then charged with nitrogen, 300 ml of cyclohexane was added and 0.5 ml of a solution of 200 mM triisobutylaluminum (Aldrich) in cyclohexane was then added. Then, after the temperature of the reactor was elevated to 140° C., 0.2 ml of bis(2-phenylphenoxy)(pentamethylcyclopentadienyl)titanium(IV) chloride (5 mM toluene solution) synthesized in Preparation Example 5 and 0.3 ml of a toluene solution of 5 mM triphenylmethylanilinium tetrakis (pentafluorophenyl)borate (99%, Boulder Scientific) were sequentially added into the reactor. Then, the reactor was charged with ethylene until the pressure within the reactor reached 30 kg/cm$^2$. Then, ethylene was continuously fed into the reactor so as to be polymerized. One minute after the start of the reaction, the temperature within the reactor reached a peak temperature of 164° C., and after 10 minutes, 10 ml of ethanol containing 10 vol % aqueous hydrochloric acid solution was added to terminate the polymerization. Then, the polymerization product was stirred in 1500 ml of ethanol for 4 hours, and the reaction product was filtered and separated. The collected reaction product was dried in a vacuum oven at 60° C., yielding 11.4 g of a polymer. The polymer had a melt index of 0.001 g/10 min, and when analyzed using gel chromatography, it showed a weight-average molecular weight (Mw) of 303,000 g/mol and a molecular weight distribution (Mw/Mn) of 3.37.

Example 4

The polymerization of ethylene was conducted at 140° C. in the same manner as in Example 3, except that 1.0 ml of a toluene solution of 100 mM modified methylaluminoxane (Akzo Nobel, modified MAO-7, 7 wt %, Al Isopar solution) was used in place of triisobutylaluminum. As a result, the peak temperature of the reaction solution was 176° C., and 14.9 g of a polymer was obtained. The polymer had a melt index of 0.10 g/10 min, and when analyzed using gel chromatography, it showed a weight-average molecular weight (Mw) of 186,000 g/mol and a molecular distribution (Mw/Mn) of 2.4.

Example 5

The polymerization of ethylene was carried out in the same manner as in Example 3, except that the initiation temperature of the polymerization was 80° C. As a result, the peak temperature of the reaction solution reached 133° C., and 25.4 g of a polymer was obtained. The melt index of the polymer was not measurable, and when analyzed using gel chromatography, the polymer had a weight-average molecular weight (Mw) of 343,000 g/mol and a molecular weight distribution (Mw/Mn) of 3.9.

Example 6

The polymerization of ethylene was carried out in the same manner as in Example 4, except that bis(4-methyl-2-(2'-isopropylphenyl)phenoxy)(pentamethylcyclopentadienyl)titanium(IV) chloride synthesized in Preparation Example 7, was used as the catalyst component. As a result, a peak temperature of 176° C. was reached and 13.6 g of a polymer was obtained. The melt index of the polymer was not measurable, and when analyzed by gel chromatography, the polymer had a weight-average molecular weight (Mw) of 299,000 g/mol and a molecular weight distribution (Mw/Mn) of 3.6.

Example 7

The polymerization of ethylene was carried out in the same manner as in Example 6, except that the initiation temperature of the polymerization was 80° C. As a result, a peak temperature of 129° C. was reached and 26.2 g of a polymer was obtained. The melt index of the polymer was not measurable, and when analyzed by gel chromatography, the polymer had a weight-average molecular weight (Mw) of 587,000 g/mol and a molecular weight distribution (Mw/Mn) of 4.7.

Example 8

Figure 3:
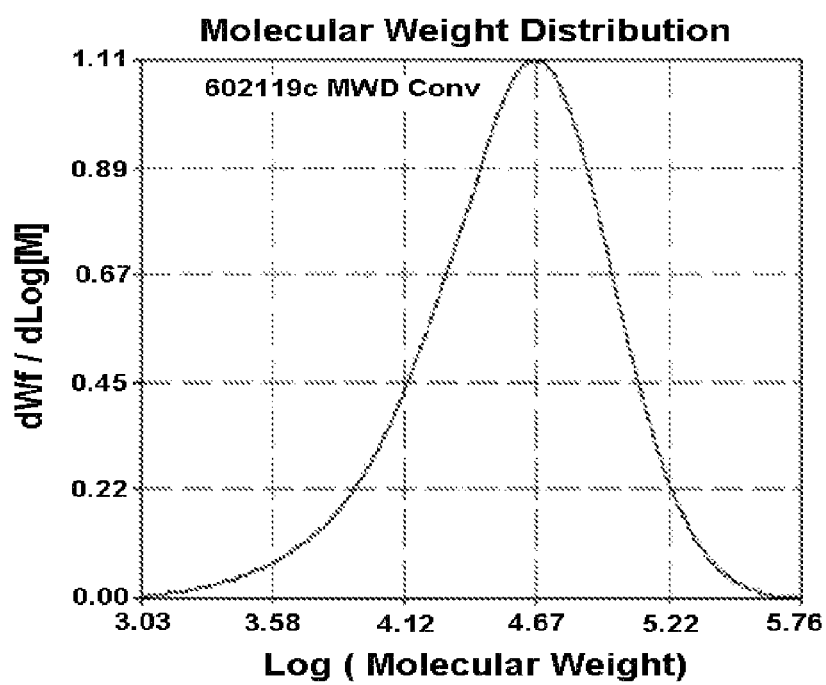
FIG. 3 shows a gel chromatography spectrum showing the molecular weight distribution of an ethylene-1-octene copolymer synthesized using a bis(phenylphenoxy)(pentamethylcyclopentadienyl)titanium (IV) chloride catalyst according to Example 8 of the present invention.
Figure 4:
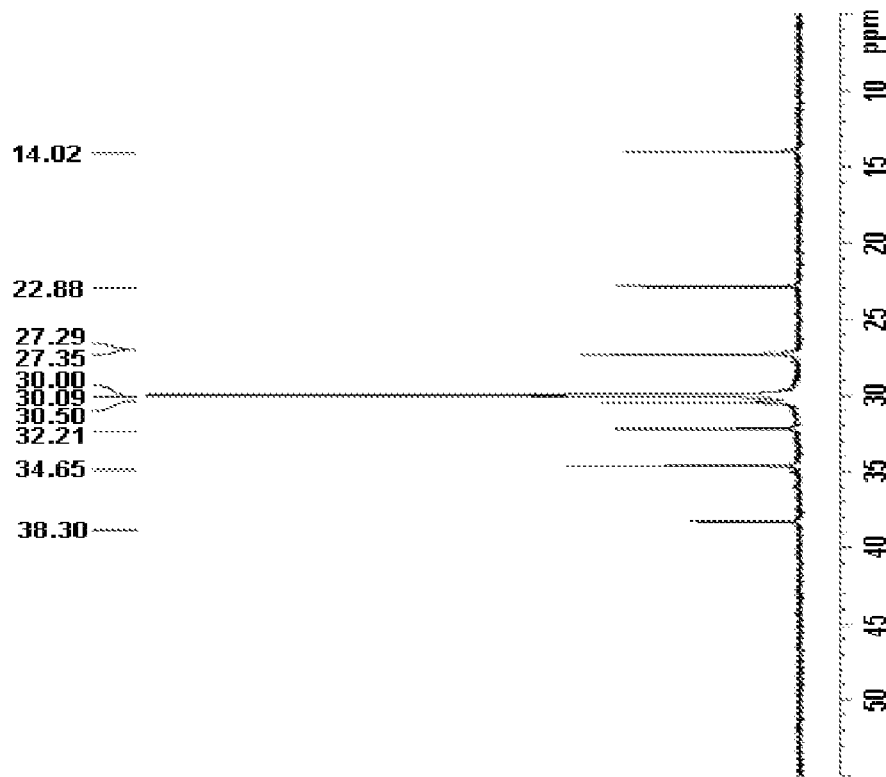
FIG. 4 shows the $^{13}$C-NMR spectrum of an ethylene-1-octene copolymer (12.9 wt % 1-octene) synthesized using a bis(phenylphenoxy)(pentamethylcyclopentadienyl)titanium (IV) chloride catalyst according to Example 8 of the present invention.

The copolymerization of ethylene with 1-octene was carried out using a continuous polymerization apparatus at high temperature. All reaction starting materials, including a catalyst, a reaction solvent and monomers, were continuously fed into a reactor by means of a metering pump, and the removal of unreacted monomers from the polymerized reaction product and the recovery of the polymer were also continuously performed. As the polymerization solvent, cyclohexane was used, and the starting materials were fed into the reactor under the following flowrate conditions: a total solution flowrate of 5.0 kg/hr, an ethylene flowrate of 0.4 kg/hr, and a 1-octene flowrate of 0.08 kg/hr. Also, the reactor was maintained at a pressure of 110 kg/cm$^2$ and a temperature of 150° C. As the catalyst, bis(2-phenylphenoxy)(pentamethylcyclopentadienyl)titanium(IV) chloride (0.7 mM toluene solution), synthesized in Preparation Example 5, was fed at a flow rate of 30 mmol Ti/hr, and as the co-catalyst, a toluene solution of 3.2 mM triphenylmethylanilinium tetrakis(pentafluorophenyl) borate (99%, Boulder Scientific) was fed at a flow rate of 60 mmol/hr. As an agent for removing impurities in the reactor and for alkylating the catalyst, a toluene solution of 31.5 mM modified methylaluminoxane-7 (Akzo Nobel, modified MAO-7, 7 wt % Al Isopar solution) was fed into the reactor at a flow rate of 0.45 mmol/hr after coming into contact with the catalyst. To the reaction product effluent from the reactor, pelargonic acid was added at a flow rate of 5.2 mmol/hr to inactivate the catalyst, and unreacted monomers and the solvent were removed, yielding a polymer. The conversion to polymer of ethylene was 95% as measured by gas chromatography, and the activity of the catalyst was 12.7 kg-PE/mmol-Ti. Analysis results for the polymer showed that the polymer had a melt index of 2.5 g/10 min, a melting point of 108° C. and a density of 0.909. As shown in FIGS. 3 and 4, the polymer had a 1-ocetene content of 12.9 wt %, and when analyzed using gel chromatography, it had a weight-average molecular weight (Mw) of 94,000 g/mol and a molecular weight distribution (Mw/Mn) of 2.3.

Example 9

The copolymerization of ethylene with 1-ocetene was carried out in a continuous reactor at 150° C. in the same manner as in Example 8, except that bis(4-methyl-2-(2'-isopropylphenyl)phenoxy)(pentamethylcyclopentadienyl)titanium (IV) chloride synthesized in Preparation Example 7 was used as the catalyst component. The conversion to polymer of ethylene was 92% as measured using gas chromatography, and the activity of the catalyst was 12.2 kg-PE/mmol-Ti. Analysis results for the polymer showed that the polymer had a melt index of 1.5 g/10 min, a melting point of 108° C., a density of 0.910, and a 1-octene content of 12.2 wt %. When analyzed using gel chromatography, the polymer had a weight-average molecular weight (Mw) of 110,000 g/mol and a molecular weight distribution (Mw/Mn) of 3.2.

Comparative Preparation Example 1

Synthesis of (2-methylphenoxy)(pentamethylcyclopentadienyl)titanium(IV) dichloride 0.86 g (5.1 mmol) of 2-methylphenol (Aldrich, 99%) was dissolved in 40 ml of toluene, and 2.4 ml of butyllithium (2.5

M hexane solution) was slowly added dropwise thereto. The mixture solution was allowed to react at room temperature for 12 hours, and a solution of (pentamethylcyclopentadienyl)titanium(IV) trichloride (1.64 g, 5.5 mmol) in 10 ml of toluene was slowly added dropwise to the reaction solution at 0° C. The reaction solution was stirred at room temperature for 12 hours, filtered, treated to remove volatile material, and recrystallized with a mixed solution of toluene and hexane at −35° C., thus obtaining 1.64 g of a red solid. The cyclic voltammogram of the catalyst thus prepared is shown in FIG. 2.

Yield: 85%, $^1$H-NMR (C$_6$D$_6$) δ=1.68 (s, 15H), 6.82-7.26 (m, 9H) ppm.

Comparative Preparation Example 2

Synthesis of tris(2-phenylphenoxy)-(pentamethylcyclopentadienyl)titanium(IV)

2.58 g (15.2 mmol) of 2-phenylphenol (Aldrich, 99%) was dissolved in 40 ml of toluene, and 7.2 ml of butyllithium (2.5M hexane solution) was slowly added dropwise thereto. The solution was allowed to react at room temperature for 12 hours, after which a solution of (pentamethylcyclopentadienyl)titanium(IV) trichloride (1.64 g, 5.5 mmol) in 10 ml of toluene was slowly added dropwise thereto at 0° C. After the mixture was stirred under toluene reflux for 12 hours, the stirred material was lowered to room temperature, filtered, treated to remove volatile material, and recrystallized with a mixed solution of toluene and hexane at −35° C., thus obtaining 3.5 g of a yellow solid. The cyclic voltammogram of the catalyst thus prepared is shown in FIG. 2.

Yield: 94%, $^1$H-NMR (C$_6$D$_6$) δ=1.43 (s, 15H), 6.82-7.26 (m, 9H) ppm.

Comparative Preparation Example 3

Synthesis of (4-methyl-2-(2'-isopropylphenyl)phenoxy)(pentamethylcyclopentadienyl)titanium(IV) dichloride 4-methyl-2-(2'-isopropylphenyl)phenol (1 g, 4.4 mmol) synthesized in Preparation Example 6 and sodium hydride (318 mg, 13.25 mmol) were dissolved in 10 ml of toluene and then allowed to react under reflux for 4 hours. After cooling the reaction solution to room temperature, a solution of (trichloro)(pentamethylcyclopentadienyl)titanium(IV) (1.15 g, 4.0 mmol) in 5 ml of toluene was slowly added dropwise to the reaction solution, and the mixture was allowed to react under reflux for 24 hours. After completion of the reaction, the reaction product was treated to remove volatile material, washed with purified pentane, and recrystallized with pentane at −35° C. The recrystallized material was filtered and dried under reduced pressure, yielding 1.53 g of a red solid.

Yield: 94%, $^1$H-NMR (C$_6$D$_6$) δ=0.96-1.07 (m, 6H), 1.76 (s, 15H), 1.89 (s, 3H), 2.99 (m, 1H), 6.85-7.37 (m, 7H) ppm.

Comparative Preparation Example 4

Synthesis of tris(4-methyl-2-(2'-isopropylphenyl)phenoxy)(pentamethyl cyclopentadienyl)titanium (IV)

4-methyl-2-(2'-isopropylphenyl)phenol (3 g, 13.2 mmol) synthesized and sodium hydride (954 mg, 39.75 mmol) were dissolved in 20 ml of toluene and then allowed to react under reflux for 4 hours. After cooling the reaction solution to room temperature, a solution of (trichloro)(pentamethylcyclopentadienyl)titanium(IV) (1.15 g, 4.0 mmol) in 5 ml of toluene was slowly added dropwise to the reaction solution, and the mixture was allowed to react under reflux for 24 hours. After completion of the reaction, the reaction product was treated to remove volatile material, washed with purified pentane, and recrystallized with pentane at −35° C. The recrystallized material was filtered and dried under reduced pressure, yielding 1.92 g of a red solid.

Yield: 57%, $^1$H-NMR (C$_6$D$_6$) δ=0.96-1.07 (m, 6H), 1.44 (s, 15H), 1.52 (s, 3H), 2.62 (m, 1H), 6.76-7.27 (m, 7H) ppm.

Comparative Example 1

The polymerization of ethylene was carried out at 140° C. in the same manner as in Example 3, except that (2-phenylphenoxy)(pentamethylcyclopentadienyl)titanium(IV) dichloride (5 mM toluene solution), synthesized in Comparative Preparation Example 1, was used. As a result, a peak temperature of 157° C. was reached, and 9.2 g of a polymer was obtained. The polymer had a melting point of 130.3° C. and a melt index of less than 0.001 g/10 min, and, when analyzed using gel chromatography, it had a weight-average molecular weight (Mw) of 246,000 g/mol and a molecular weight distribution (Mw/Mn) of 3.6.

Comparative Example 2

The polymerization of ethylene was performed at 140° C. in the same manner as in Comparative Example 1, except that 1.0 ml of a toluene solution of 100 mM modified aluminoxane-7 (Akzo Nobel, modified MAO-7, 7 wt % Al Isopar solution) was added in place of triisobutyl aluminum. As a result, a peak temperature of 163° C. was reached, and 7.4 g of a polymer was obtained. The polymer had a melt index of 0.001 g/10 min, and when analyzed using gel chromatography, it had a weight-average molecular weight (Mw) of 197,000 g/mol and a molecular weight distribution (Mw/Mn) of 2.2.

Comparative Example 3

The polymerization of ethylene was carried out in the same manner as in Comparative Example 1, except that the initiation temperature of the polymerization was 80° C. As a result, a peak temperature of 119° C. was reached and 11.3 g of a polymer was obtained. The polymer had a melt index of less than 0.001 g/10 min, and when analyzed using gel chromatography, it had a weight-average molecular weight (Mw) of 264,000 g/mol and a molecular weight distribution (Mw/Mn) of 4.5.

Comparative Example 4

The polymerization of ethylene was carried out at 140° C. in the same manner as in Comparative Example 1, except that 0.2 ml of tris(2-phenylphenoxy)(pentamethylcyclopentadienyl)titanium(IV) (5 mM toluene solution) synthesized in Comparative Preparation Example 2 was used as the catalyst component. As a result, a peak temperature of 156° C. was reached and 8.5 g of a polymer was obtained. The polymer had a melting point of 131.0°C., and the melt index thereof was not measurable. When analyzed using gel chromatography, the polymer had a weight-average molecular weight (Mw) of 228,000 g/mol and a molecular weight distribution (Mw/Mn) of 2.9.

Comparative Example 5

The polymerization of ethylene was carried out in the same manner as in Comparative Example 4, except that the initiation temperature of the polymerization was 80° C. As a result, a peak temperature of 127° C. was reached and 14.3 g of a polymer was obtained. The melt index of the polymer was not measurable, and when analyzed using gel chromatography, the polymer had a weight-average molecular weight (Mw) of 297,000 g/mol and a molecular weight distribution (Mw/Mn) of 5.6.

Comparative Example 6

The polymerization of ethylene was carried out at 140° C. in the same manner as in Comparative Example 2, except that 0.2 ml of 4-methyl-2-(2'-isopropylphenyl)phenoxy)(pentamethylcyclopentadienyl)titanium(IV) dichloride (5 mM toluene solution) synthesized in Comparative Preparation Example 3 was used as the catalyst. As a result, a peak temperature of 150° C. was reached, and 6.0 g of a polymer was obtained. The polymer had a melt index of less than 0.05 g/10 min, and, when analyzed using gel chromatography, it had a weight-average molecular weight (Mw) of 214,000 g/mol and a molecular weight distribution (Mw/Mn) of 2.5.

Comparative Example 7

The polymerization of ethylene was carried out in the same manner as in Comparative Example 6, except that the initiation temperature of the polymerization was 80° C. As a result, a peak temperature of 108° C. was reached and 14.3 g of a polymer was obtained. The polymer had a melt index of less than 0.001 g/10 min, and, when analyzed using gel chromatography, it had a weight-average molecular weight (Mw) of 673,000 g/mol and a molecular weight distribution (Mw/Mn) of 2.8.

Comparative Example 8

The polymerization of ethylene was carried out at 140° C. in the same manner as in Comparative Example 2, except that 0.2 ml of (tris(4-methyl-2-(2'-isopropylphenyl)phenoxy)(pentamethylcyclopentadienyl)titanium(IV) (5 mM toluene solution), synthesized in Comparative Preparation Example 4, was used as the catalyst. As a result, a peak temperature of 156° C. was reached, and 5.8 g of a polymer was obtained. The polymer had a melt index of less than 0.03 g/10 min, and, when analyzed using gel chromatography, it had a weight-average molecular weight (Mw) of 205,000 g/mol and a molecular weight distribution (Mw/Mn) of 2.7.

Comparative Example 9

The polymerization of ethylene was carried out in the same manner as in Comparative Example 1, except that 0.2 ml of (trimethyl)(pentamethylcyclopentadienyl)titanium(IV) (97%, Strem, 5 mM toluene solution) was used as the catalyst, thus obtaining 1.1 g of a polymer. The polymer had a melt index of less than 0.16 g/10 min, and, when analyzed using gel chromatography, it had a weight-average molecular weight (Mw) of 150,000 g/mol and a molecular weight distribution (Mw/Mn) of 5.5.

Comparative Example 10

The polymerization of ethylene was carried out in the same manner as in Comparative Example 1, except that 0.2 ml of rac-dimethylsilylbis(2-methylindenyl)zirconium dichloride (5 mM toluene solution; Boulder Scientific) was used as the catalyst. The polymerization product was dried, yielding 15.0 g of a polymer. The polymer had a melting point of 123.2° C. and a melt index of 110 g/10 min, and when analyzed using gel chromatography, it had a weight-average molecular weight (Mw) of 28,000 g/mol and a molecular weight distribution (Mw/Mn) of 12.0.

As apparent from the above description, The bis-arylaryloxy catalyst system according to the present invention is easy to handle, is prepared using eco-friendly raw-materials, and is also synthesized using a simple process, so that it can produce ethylene homopolymers or copolymers at high yield in an economic manner. Also, the catalyst has excellent thermal stability, and thus has good copolymerization reactivity with higher α-olefins while maintaining high catalytic activity even in high-temperature solution polymerization conditions, and can produce high-molecular-weight polymers. Thus, the catalyst system according to the present invention has high utility compared to previously known metallocene or non-metallocene single-active-site catalysts. Accordingly, the bis-arylaryloxy catalyst system according to the present invention is useful for the production of ethylene homopolymers or ethylene/α-olefin copolymers, which have various physical properties.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A bis-arylaryloxy transition metal catalyst shown in Formula 1, which comprises a cyclopentadienyl group containing ligand around a transition metal and two aryloxide ligands substituted with aryl derivatives at the ortho-positions, the ligands not being bridged to each other:

[Formula 1]

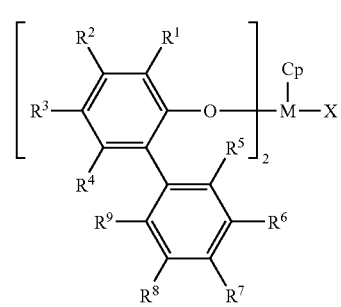

wherein M is a group-IV transition metal in the periodic table; Cp is cyclopentadienyl or a derivative thereof, which forms an $\eta^5$ bond with the central metal; $R^1, R^2, R^3, R^4, R^5, R^6, R^7, R^8$ and $R^9$ on the arylphenoxide ligands are each independently a hydrogen atom, a halogen atom, a C1-C20 linear or nonlinear alkyl group optionally substituted with at least one halogen atoms, a silyl group containing a C1-C20 linear or nonlinear alkyl group optionally substituted with at least one halogen atoms, a C6-C30 aryl group optionally substituted with at least one halogen atom, a C7-C30 arylalkyl group optionally substituted with at least one halogen atom, an alkoxy group having a C1-C20 linear or nonlinear alkyl group optionally substituted with at least one halogen atoms, a siloxy group having C3-C20 alkyl or C6-C20 aryl, an amido or phosphido group having a C1-C20 hydrocarbon group, or a mercapto group having C1-C20 alkyl, or a nitro group, and these substituents ma y also optionally bind to each other to form a ring; and X is selected from the group consisting of an halogen atom, a C1-C20 alkyl group other than a Cp derivative, a C7-C30 arylalkyl group, an alkoxy group having a C1-C20 alkyl group, a siloxy group substituted with C3-C20 alkyl, and an amido group having a C1-C20 hydrocarbon group.

2. The bis-arylaryloxy transition metal catalyst of claim 1, wherein said M is titanium.

3. The bis-arylaryloxy transition metal catalyst of claim 1, wherein said Cp is selected from among cyclopentadienyl and pentamethylcyclopentadienyl.

4. The bis-arylaryloxy transition metal catalyst of claim 1, wherein said $R^1$, $R^2$, $R^3$, $R^4$, $R^5$, $R^6$, $R^7 R^8$ and $R^9$ on the arylphenoxide ligands are each individually selected from among a hydrogen atom, a methyl group and an isopropyl group.

5. The bis-arylaryloxy transition metal catalyst of claim 1, wherein said X is selected from among a chlorine atom, a methyl group, a methoxy group, an isopropoxy group and a dimethylamino group.

6. A bis-arylaryloxy catalyst system for producing ethylene homopolymers or ethylene and α-olefin copolymers, comprising: a bis-arylaryloxy transition metal catalyst of Formula 1 containing a cyclopentadienyl group containing ligand around a transition metal and two aryloxide ligands substituted with aryl derivatives at the ortho-positions, the ligands not being bridged to each other; and an aluminoxane co-catalyst or a boron compound cocatalyst:

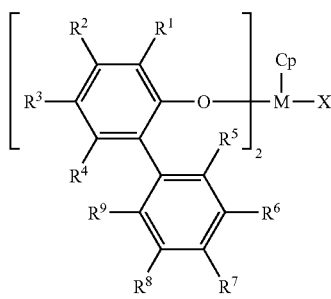

[Formula 1]

wherein M is a group-IV transition metal in the periodic table; Cp is cyclopentadienyl or a derivative thereof, which forms an $\eta^5$ bond with the central metal; $R^1$, $R^2$, $R^3$, $R^4$, $R^5$, $R^6$, $R^7$, $R^8$ and $R^9$ on the arylphenoxide ligands are each independently a hydrogen atom, a halogen atom, a C1-C20 linear or nonlinear alkyl group optionally substituted with at least one halogen atoms, a silyl group containing a C1-C20 linear or nonlinear alkyl group optionally substituted with at least one halogen atoms, a C6-C30 aryl group optionally substituted with at least one halogen atom, a C7-C30 arylalkyl group optionally substituted with at least one halogen atom, an alkoxy group having a C1-C20 linear or nonlinear alkyl group optionally substituted with at least one halogen atom, a siloxy group having C3-C20 alkyl or C6-C20 aryl, an amido or phosphido group having a C1-C20 hydrocarbon group, or a mercapto group having C1-C20 alkyl, or a nitro group, and these substituents ma y also optionally bind to each other to form a ring; and X is selected from the group consisting of an halogen atom, a C1-C20 alkyl group other than a Cp derivative, a C7-C30 arylalkyl group, an alkoxy group having a C1-C20 alkyl group, a siloxy group substituted with C3-C20 alkyl, and an amido group having a C1-C20 hydrocarbon group.

7. The bis-arylaryloxy catalyst system of claim 6, wherein the aluminoxane cocatalyst is methylaluminoxane, and is used in a molar ratio of central metal:aluminum of 1:50 to 1:5,000.

8. The bis-arylaryloxy catalyst system of claim 6, wherein the boron compound co-catalyst is selected from among N,N-dimethylanilinium tetrakispentafluorophenylborate and triphenylmethylanilinium tetrakispentafluorophenylborate.

9. The bis-arylaryloxy catalyst system of claim 6, wherein the boron compound co-catalyst is used in a mixture with aluminoxane or organoalkylaluminum such that the molar ratio of central metal:boron atom:aluminum atom is 1:0.5-5:25-500.

10. The bis-arylaryloxy catalyst system of claim 9, wherein the aluminoxane is methylaluminoxane, and the organoalkylaluminium is selected from among triethylaluminum and triisobutylaluminum.

11. A method for producing a copolymer of ethylene with α-olefin using the bisarylaryloxy catalyst system of claim 6, in which the comonomer α-olefin for polymerization with ethylene is at least one selected from the group consisting of 1-butene, 1-hexene, 1-octene, and 1-decene, and the content of ethylene in the ethylene/α-olefin copolymer is more than 60 wt %.

12. A method for producing an ethylene homopolymer or an ethylene copolymer with α-olefin using the bis-arylaryloxy transition metal catalyst of claim 1, in which the pressure of the ethylene monomer in a reactor is 10-150 atm, and the polymerization of the ethylene monomer is conducted at 80-250° C.

* * * * *

UNITED STATES PATENT AND TRADEMARK OFFICE
CERTIFICATE OF CORRECTION

| | | |
|---|---|---|
| PATENT NO. | : 7,645,715 B2 | Page 1 of 1 |
| APPLICATION NO. | : 11/738697 | |
| DATED | : January 12, 2010 | |
| INVENTOR(S) | : Myung Ahn Ok et al. | |

It is certified that error appears in the above-identified patent and that said Letters Patent is hereby corrected as shown below:

On the title page, item [75], in "Inventors", line 4, delete "Tae Eung Kim, Seoul (KR)" and insert -- Tae Jin Kim, Seoul (KR) --.

Signed and Sealed this

Sixteenth Day of February, 2010

David J. Kappos
*Director of the United States Patent and Trademark Office*